United States Patent
Otani et al.

(10) Patent No.: US 8,492,146 B2
(45) Date of Patent: Jul. 23, 2013

(54) PROCESS FOR PRODUCING A HUMAN T-CELL POPULATION HAVING BOTH CYTOTOXIC AND IMMUNOSUPPRESSIVE ACTIVITIES

(75) Inventors: Takeshi Otani, Okayama (JP); Makoto Takeuchi, Okayama (JP); Shuji Nakamura, Okayama (JP); Fumiyuki Yamasaki, Okayama (JP)

(73) Assignee: Hayashibara Co., Ltd., Okayama (JP)

( * ) Notice: Subject to any disclaimer, the term of this patent is extended or adjusted under 35 U.S.C. 154(b) by 0 days.

(21) Appl. No.: 13/265,942

(22) PCT Filed: Apr. 15, 2010

(86) PCT No.: PCT/JP2010/056770
§ 371 (c)(1),
(2), (4) Date: Oct. 24, 2011

(87) PCT Pub. No.: WO2010/122945
PCT Pub. Date: Oct. 28, 2010

(65) Prior Publication Data
US 2012/0040454 A1    Feb. 16, 2012

(30) Foreign Application Priority Data
Apr. 24, 2009 (JP) ................... 2009-106311

(51) Int. Cl.
*C12N 5/0783* (2010.01)
(52) U.S. Cl.
USPC ............. 435/372.3; 435/347; 424/93.71
(58) Field of Classification Search
None
See application file for complete search history.

(56) References Cited

U.S. PATENT DOCUMENTS

| 4,963,489 A | * | 10/1990 | Naughton et al. | ............ 435/1.1 |
| 7,211,432 B2 | * | 5/2007 | Schlom et al. | ............ 435/320.1 |
| 2009/0297490 A1 | | 12/2009 | Nakamura et al. | |

FOREIGN PATENT DOCUMENTS

| EP | 1997884 A1 | 12/2008 |
| JP | 2005245430 A | 5/2005 |
| KR | 10-2008-0111054 A | 12/2008 |
| WO | 2007105797 A1 | 9/2007 |

OTHER PUBLICATIONS

Nakamura S et al. IL-2-independent generation of FOXP3(+)CD4(+)CD8(+)CD25(+) cytotoxic regulatory T cell lines from human umbilical cord blood. Exp Hematol. Feb. 2007;35(2):287-96.*
Nakamura S et al. (2007). IL-2-independent generation of FOXP3+CD4+CD8+CD25+ cytotoxic regulatory T cell lines from human umbilical cord blood. Experimental Hematology, v35, p. 287-296.*
Takamizawa M et al. (1997) Dendritic Cells that Process and Present Nominal Antigens to Naive T Lymphocytes are derived from CD2+ Precursors. The Journal of Immunology, v158(5), p. 2134-2142.*
Ujam LB et al. (2003). Isolation of Monocytes from Human Peripheral Blood Using Immuno-Affinity Expanded-Bed Adsorption. Biotechnology and Bioengineering, v83(5), p. 554-566.*

(Continued)

*Primary Examiner* — Sharmila G. Landau
*Assistant Examiner* — Sean C Barron
(74) *Attorney, Agent, or Firm* — Browdy and Neimark, PLLC

(57) ABSTRACT

A human T cell population which has both cytotoxic and immunosuppressive activities, is efficiently produced by first fractionating CD2-positive CD14-negative cells from mononuclear cells collected from a human umbilical cord blood, and then co-culturing them with stromal cells. The resulting blast cells, which have the desired activity, are proliferated by further culture.

2 Claims, 3 Drawing Sheets

OTHER PUBLICATIONS

International Search Report issued by the Japanese Patent Office in Patent Application No. PCT/JP2010/056770 on Jun. 14, 2010.

Sakaguchi, Shimon, "Naturally Arising CD4+ Regulatory T Cells for Immunologic Self-Tolerance and Negative Control of Immune Responses", Annual Review of Immunology, vol. 22, pp. 531-562, 2004.

Fontenot, Jason D. et al., "Foxp3 programs the development and function of CD4+CD25+ regulatory T Cells", Nature Immunology, Nature Publishing Group, vol. 4, No. 4, pp. 330-336, Apr. 2003.

Takahashi, Takeshi et al., "Immunologic Self-Tolerance Maintained by CD25+CD4+ Regulatory T Cells Constitutively Expressing Cytotoxic T Lymphocyte-associated antigen 4", The Journal of Experimental Medicine, The Rockefeller University Press, vol. 192, No. 2, pp. 303-309, Jul. 2000.

Cosmi, Lorenzo et al., "Human CD8+CD25+ thymocytes share phenotypic and functional features with CD4+CD25+ regulatory thymocytes", Immunobiology, blood, vol. 102, No. 12, pp. 4107-4114, Dec. 2003.

Godfrey, Wayne R. et al., "In vitro-expanded human CD4+CD25+ T-regulatory cells can markedly inhibit allogeneic dendritic cell-stimulated MLR cultures", blood, vol. 104, No. 2, pp. 453-461, 2004.

Imataki, Osamu et al., "Insufficient Ex Vivo Expansion of V-alpha-24+ Natural Killer T Cells in Cancer Patients May Be Related to the Suppressed Expression of CD1d Molecules on CD14+ Cells", blood, Abstract 1066, 2005.

Miller, Jeffrey S. et al., "The Generation of Human Natural Killer Cells from CD34+/DR—Primitive Progenitors in Long-Term Bone Marrow Culture", blood, vol. 80, No. 9, pp. 2182-2187, 1992.

Toka, Felix N. et al., "Activation of Porcine Natural Killer Cells and Lysis of Foot-and-Mouth Disease Virus Infected Cells", Journal of Interferon & Cytokine Research, vol. 29, No. 3, pp. 179-192, 2009.

Tschiedel, Sabine et al., "An Immunogenic Peptide Derived from NM32-H2 Is Expressed on Bcr/abl+ Cells", blood, Abstract 3684, 2006.

* cited by examiner

PROCESS FOR PRODUCING A HUMAN T-CELL POPULATION HAVING BOTH CYTOTOXIC AND IMMUNOSUPPRESSIVE ACTIVITIES

TECHNICAL FIELD

The present invention relates to a method for producing a human T cell population which has both cytotoxic and immunosuppressive activities, more particularly, to a method for producing a human T cell population which has both cytotoxic and immunosuppressive activities, comprising the following steps (1) to (4):

(1) fractionating mononuclear cells collected from a human umbilical cord blood into CD14-positive ($CD^+$) cells and CD14-negative ($CD14^-$) cells, and then fractionating the CD14-negative ($CD14^-$) cells into CD2-positive CD14-negative ($CD2^+CD14^-$) cells and CD2-negative CD14-negative ($CD2^-CD14^-$) cells;

(2) co-culturing the CD2-positive CD14-negative ($CD2^+CD14^-$ cells obtained in step (1) with stromal cells to generate blast cells;

(3) adding the blast cells obtained in step (2) to the co-culture of the CD14-positive ($CD14^+$) cells obtained in step (1) with stromal cells to allow the blast cells to proliferate; and (4) allowing the blast cells obtained in step (3) to further proliferate by co-culturing with stromal cells in the presence of interleukin-2 (IL-2) to generate a human T cell population which has both cytotoxic and immunosuppressive activities.

BACKGROUND ART

T Cells are one of cell populations which play a major central role in immune system as a biological defense system against various pathogens. Such T cells are roughly classified into CD4-positive helper T cells and CD8-positive cytotoxic T cells. The former relates to the promotion of immune response and the latter relates to the exclusion of virus-infected-cells and tumor cells. Helper T cells are further classified into both T helper type 1 cells which promote cell-mediated immunity and T helper type 2 cells which promote humoral immunity. These T cells with such different properties have functions of excluding pathogens and of acquiring infection tolerance under well-balanced immune response.

Usually, under the normal immune response, no exclusion system functions because immunological tolerance against self-antigens that constitute living bodies has already been established. Self-reactive T cells induce either cell death or non-reaction against self-antigens. In particular, it has been said that regulatory T cells positively relate to such regulation. Such regulatory T cells are defined as those which have function of suppressing other T cells and, recently, they have been researched as a cell population with function of suppressing a particular immune response, reporting that there exist different types of regulatory T cells with different cell-surface markers, producing cytokines, immunosuppressive mechanisms, etc.

Among these regulatory T cells, most well-studied are, for example, CD4-positive CD25-positive regulatory T cells ($CD4^+CD25^+$ Treg cells), disclosed by Sakaguchi in "*Annual review of immunology*", Vol. 22, pp. 531-562, 2004. In the past results in many researches, since the above cells exhibit CD4-positive CD25-positive features, CD4 and CD25 are recognized to be used as markers for regulatory T cells. As for CD4-positive CD25-positive regulatory T cells, Fontenot et al., "*Nature immunology*", Vol. 4, No. 4, pp. 330-336, 2003, discloses "FOXP3", a transcription factor; and Takahashi et al., "*Journal of experimental medicine*", Vol. 192, No. 2, pp. 303-309, 2000, discloses "CTLA-4", a cytolytic T lymphocyte associated antigen-4, which induces T cells into unreactive conditions. Cosmi et al., "*Blood*", Vol. 102, No. 12, pp. 4107-4114, 2003, discloses a T cell having a CD8-positive CD25-positive marker and immunosuppressive activity.

As described above, CD8-positive cytotoxic T cells are well known as T cells having cytotoxic activity, which show a relatively high specific, cytotoxic activity against target cells. Japanese Patent Kokai No. 2005-245430 discloses that CD8-positive cytotoxic T cells exert a specific, cytotoxic activity against tumor cells when co-cultured with them or a protein characteristic to them.

International Patent Publication No. WO 2007/105797 A1 applied for by the same applicant as the present invention discloses that there can be obtained a novel human T cell population, which exerts cytotoxic and immunosuppressive activities against activated human T cells when mononuclear cells collected from human blood are co-cultured with stromal cells. The human T cell population is expected for use in researches and medicals because substantially most of the cells in the T cell population are positive for cell-surface-antigens CD3, CD25, and CD28 and for T cell antigen receptor $\alpha/\beta$; contain all three groups of a CD4-positive CD8-positive T cell group, CD4-positive CD8-dimly positive T cell group, and CD4-negative CD8-positive group; and have both cytotoxic and immunosuppressive activities.

The method for producing a T cell population, which has both cytotoxic and immunosuppressive activities disclosed in International Patent Publication No. WO 2007/105797 A1 (hereinafter, the method is described as "conventional method" throughout the specification), is a simple method containing the steps of continuously co-culturing mononuclear cells collected from a fresh umbilical cord blood or peripheral blood in the absence of IL-2, co-culturing the generated blast cells with stromal cells in the presence of IL-2, and further proliferating the resulting cells to form a desired T cell human population which has both cytotoxic and immunosuppressive activities. The conventional method, however, requires mononuclear cells derived from a fresh human umbilical cord blood or peripheral blood and needs a long period of time, i.e., three to four weeks, to induce and proliferate blast cells. In practicing the conventional method, the following drawbacks are still remained; a fresh umbilical cord blood or peripheral blood is inevitable, a long culturing period of about four weeks is needed, and a possible percentage of inducing a desired human T cell population is usually low, i.e., about 10% (one out of ten populations). Any industrially applicable method for producing the same has not been established yet. Under these circumstances, there required is the establishment of a method for efficiently producing a desired human T cell population, which has both cytotoxic and immunosuppressive activities, disclosed in International Patent Publication No. WO 2007/105797 A1.

DISCLOSURE OF INVENTION

In view of these circumstances, the present invention has an object to provide a method for efficiently producing a human T cell population which has both cytotoxic and immunosuppressive activities.

The present inventors diligently studied a method for efficiently producing such a human T cell population which has both cytotoxic and immunosuppressive activities, particularly, to a method for culturing the same, and they revealed the following and established the present invention:

(A) a human T cell population, which has both cytotoxic and immunosuppressive activities, is produced at a relatively high efficiency by collecting CD14-positive cells and CD2-positive CD14-negative cells, and then co-culturing the CD2-positive CD14-negative cells with stromal cells to generate blast-transformed cells (blast cells), adding the resulting blast cells to a culture which has been prepared by co-culturing the above-collected CD14-positive cells with stromal cells to allow the blast cells to proliferate, and further co-culturing the blast cells with stromal cells in the presence of interleukin-2 (IL-2) to further proliferate the blast cells, (B) unlike conventional method, there is no need for preparing mononuclear cells in obtaining a fresh human umbilical cord blood or peripheral blood at every time when producing a desired human T cell population, because the above CD14-positive cells and CD2-positive CD14-negative cells can be cryopreserved and the cryopreserved cells can be used after thawing whenever the desired human T cell population is prepared; and (C) according to the presently established method for production, the desired human T cell population which has both cytotoxic and immunosuppressive activities can be prepared in a shorter period of time than that of conventional method.

The present invention solves the above object by providing the method for producing a human T cell population which has both cytotoxic and immunosuppressive activities, which has the following steps (1) to (4):

(1) fractionating mononuclear cells collected from a human umbilical cord blood into CD14-positive (CD14$^+$) cells and CD14-negative (CD14$^-$) cells, and then fractionating the CD14-negative (CD14$^-$) cells into CD2-positive CD14-negative (CD2$^+$CD14$^-$) cells and CD2-negative CD14-negative (CD2$^-$CD14$^-$) cells;

(2) co-culturing the CD2-positive CD14-negative (CD2$^+$CD14$^-$) cells obtained in step (1) with stromal cells to generate blast cells;

(3) adding the blast cells obtained in step (2) to the co-culture of the CD14-positive (CD14$^+$) cells obtained in step (1) with stromal cells to allow the blast cells to proliferate; and (4) allowing the blast cells obtained in step (3) to further proliferate by co-culturing with stromal cells in the presence of interleukin-2 (IL-2) to generate a human T cell population which has both cytotoxic and immunosuppressive activities.

According to the present invention, a human T cell population, which has both cytotoxic and immunosuppressive activities and which is useful for research applications and medical uses for treating cancer diseases, autoimmune diseases, and allergic diseases; and those for relieving rejection reactions in transplantation and graft-versus-host-reaction, is efficiently produced.

BEST MODE FOR CARRYING OUT THE INVENTION

Figure 1:
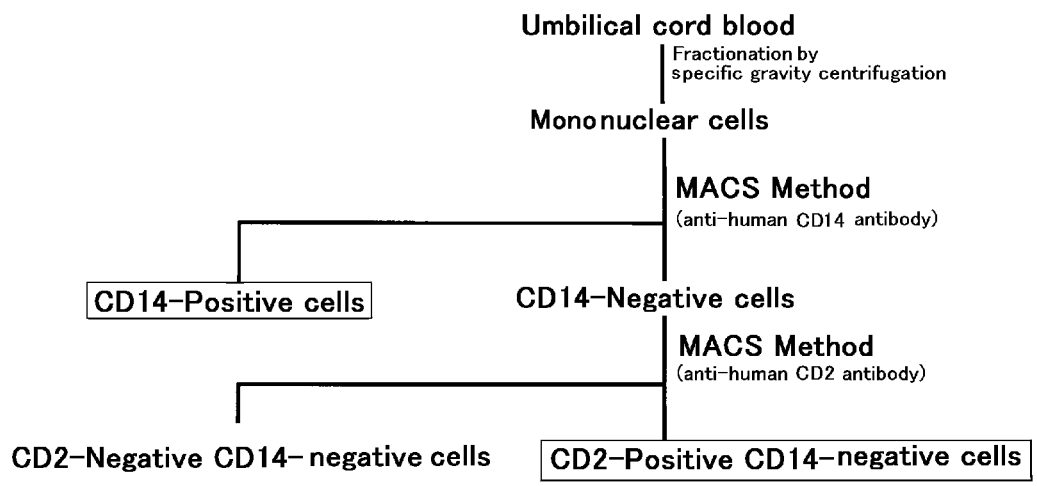
FIG. 1 is a figure for typically explaining the first step in the production method according to the present invention.

The present invention relates to a method for efficiently producing a human T cell population which has both cytotoxic and immunosuppressive activities, disclosed in International Patent Publication No. WO 2007/105797 A1 applied for by the same applicant as the present invention. The term "a human T cell population which has both cytotoxic and immunosuppressive activities" as referred to as in the present invention means a human T cell population obtainable by co-culturing mononuclear cells collected from human blood with stromal cells disclosed in International Patent Publication No. WO 2007/105797A1, and means those which are characterized by the following features (1) to (5):

(1) being positive for cell-surface-antigens CD3, CD25 and CD28, as well as for T cell antigen receptor $\alpha/\beta$;

(2) substantially consisting of three groups of a CD4-positive CD8-positive T cell group, CD4-positive CD8-dimly positive T cell group, and CD4-negative CD8-positive T cell group;

(3) exerting cytotoxic activity against stromal cells used in co-culturing;

(4) exerting immunosuppressive activity against activated T cells; and (5) producing interleukin-10 (IL-10) in the presence of interleukin-2 (IL-2).

In the first step of the production method according to the present invention, mononuclear cells are firstly collected from human umbilical cord blood, and then fractionating the mononuclear cells into CD14-positive cells and CD14-negative cells in terms of cell-surface-antigens, and then fractionating the CD14-negative cells into CD2-positive CD14-negative cells and CD2-negative CD14-negative cells. Human umbilical cord blood has become to be easily collected under an informed consent as the recently prevailed transplantation technology for umbilical cord blood. Examples of the method for collecting mononuclear cells from human umbilical cord blood include conventional density-gradient-centrifugation using FICOLL-PAQUE™ PLUS, a trademark for a density reparatory liquid for lymphocytes, commercialized by GE Healthcare Biosciences, Tokyo, Japan. The collected mononuclear cells can be cultured in conventional manner by using media for blood cells, for example, D-MEM medium, α-MEM medium, RPMI1640 medium, etc. If necessary, any medium, supplemented with fetal calf serum albumin at an appropriate concentration, can be used.

Examples of the method for fractionating mononuclear cells from umbilical cord blood into CD14-positive cells and CD14-negative cells include conventional MACS (Magnetic activated cell sorting) method can be advantageously used. Explaining briefly the MACS method, firstly, a solution containing mononuclear cells is admixed with magnetized microbeads coupled with an anti-human CD14 monoclonal antibody to allow only CD14-positive cells to be magnetized for labeling. Secondary, the magnetized CD14-positive cells are specifically adsorbed onto a column installed with magnet and the remaining unlabelled, non-magnetized CD14-negative cells are eluted from the column. The magnet is removed from the column to allow the CD14-positive cells to elute from the column. Further, the above CD14-negative cells can be fractionated into CD2-positive CD14-negative cells and CD2-negative CD14-negative cells by applying the above-identified MACS method using microbeads coupled with an anti-human CD2 monoclonal antibody.

The second step in the production method according to the present invention is a step for generating blast cells by co-culturing the CD2-positive CD14-negative cells, which have been obtained in the above first step, with stromal cells. In the production method according to the present invention, co-culturing of CD2-positive CD14-negative cells with stromal cells is essential, and examples of the stromal cells include commercialized mouse stromal cell strains, for example, ST2 cells, OP9 cells, and MC-3T3-G2/PA6 cells, which are easily available and advantageously used. If necessary, stromal cells can be collected from mice. Other stromal cells, derived from mammals other than mice, such as human stromal cells can be used. Prior to use, stromal cells are inoculated to microplates, etc., along with appropriate culture media, and then cultured for one to several days until the cells proliferate over the surface of the well's bottoms of microplates to confluent states. CD2-Positive CD14-negative cells are inoculated to the resulting culture before incubating at 37° C. under 5% $CO_2$ atmospheric conditions to allow the CD2-positive CD14-negative cells to partly generate into blast-transformed cells, resulting in forming a cell population which contains blast cells with cytotoxic activity, while gradually decreasing viable stromal cells. In the second step, however, CD2-positive CD14-negative cells can be differentiated into blast cells but such cells could not be proliferated in large quantities.

In the second step in the production method according to the present invention, when co-culturing with stromal cells, CD2-positive CD14-negative cells should preferably be adjust to give a relatively high density of at least $6 \times 10^6$ cells per one well of a microplate (3 ml, bottom surface area of 9.62 $cm^2$) or at least $6.2 \times 10^5/cm^2$, based on the bottom surface area of each well. When the cell density is set to a relatively low level of $2 \times 10^6$ cells per one well (3 ml) or about $2.1 \times 10^5$ cells/$cm^2$, based on the bottom surface area of each well, the cell count of blast cells generated by co-culturing with stromal cells becomes less, while the rate of blast cells in the total cells in the formed human cell population lowers and the production efficiency is deteriorated.

The third step in the production method according to the present invention is a step for adding either cells containing blast cells obtained in the second step or purified ones thereof cells through density-gradient-centrifugation, etc., to a cell culture, which has been previously co-culturing the CD14-positive cells obtained in the first step, with stromal cells similarly as in the above second step, and further co-culturing the resultant to proliferate the blast cells. The CD14-positive cells differentiate into cells capable of promoting the proliferation of the blast cells through co-culturing with the stromal cells, however, the CD14-positive cells per se are not generated into blast-transformed cells. Since the proliferation of blast cells are suppressed when stromal cells are totally destroyed during the co-culturing of the stromal cells and the blast cells, the blast cells should necessarily be transferred to another microplate adhered to which stromal cells are adhered. In the transferring, after initiating the proliferation of floating blast cells, such floating cells are successively collected with a pipette, etc., at an interval of two to three days, followed by transferring the collected cells to another microplate, to which fresh stromal cells are adhered, and continuing the co-culture. In this step, even if the inoculated blast cells were contaminated with cells in resting stage which have not been generated into blast-transformed cells in the previous step, such cells will be extinguished (dead) during the following co-culturing and finally only blast cells are remained. Accordingly, blast cells are obtained in an increased cell count by about 3- to 15-folds to that of the inoculated cells after six to nine days of continuous culturing.

The fourth step in the production method according to the present invention is a step for co-culturing the blast cells, which have been proliferated in the above-mentioned third step, with stromal cells in the presence of IL-2 to further proliferate and to obtain a desired human T cell population which has both cytotoxic and immunosuppressive activities. Since IL-2 proliferates IL-2-dependent-activated-T-cells present in cells derived from blood, cells are cultured in the absence of IL-2 so as not to proliferate activated T cells in the above-mentioned second and third steps; however, in the fourth step, cells can be cultured for proliferation in the presence of IL-2 up to increase the cell count by about 7- to 400-folds of that of the initially inoculated cells because the cells consist of blast cells at this stage of the fourth step. In this step of co-culturing blast cells with stromal cells in the presence of IL-2, the blast cells can be differentiated into a desired human T cell population which has both cytotoxic and immunosuppressive activities.

According to the production method containing the above-mentioned four steps, a human T cell population which has both cytotoxic and immunosuppressive activities is efficiently produced. In the present production method, since the once-obtained CD14-positive cells and CD2-positive CD14-negative cells can be cryopreserved, they can be appropriately thawed, depending on use; and therefore a human T cell population which has both cytotoxic and immunosuppressive activities can be prepared without a need of freshly prepared mononuclear cells from human umbilical cord blood or peripheral blood in each preparation.

The following criteria are to judge whether a human T cell population, prepared by the production method according to the present invention, is a desired human T cell population which has both cytotoxic and immunosuppressive activities:
(1) CD4-Positive CD8-positive T cells account for at least 20% of the total cells;
(2) It exhibits cytotoxic activity against stromal cells used in previous co-culturing;
(3) It exhibits cytotoxic activity against WiDr cell strain derived from human colon cancer;
(4) It has immunosuppressive activity against activated T cells;
(5) It is positive for cell-surface-antigens CD3, CD25 and CD28, as well as T cell antigen receptor $\alpha/\beta$; and
(6) It produces IL-10 in the presence of IL-2.

Among the above, (2) and (4) to (6) are characteristics of the human T cell population, which has both cytotoxic and immunosuppressive activities, disclosed in International Patent Publication No. WO 2007/105797 A1; while (1) and (3) are the criteria newly settled in the present invention.

The human T cell population which has both cytotoxic and immunosuppressive activities, obtained by the production method according to the present invention, consists essentially of CD4-positive CD8-positive cells (A group), CD4-positive CD8-dimly positive cells (B group), and CD4-negative CD8-positive (C group), and the total cell count of the above three groups is at least 90%, preferably, at least 95% to the total cell count of the human T cell population. The term "human T cell population which has both cytotoxic and immunosuppressive activities" as referred to as in the present invention, is characterized in that it is a human T cell population which contains a relatively large amount of CD4-positive CD8-positive T cells (A group), preferably, the one which contains CD4-positive CD8-positive T cells in an amount of at least 20% to the total cells of the human T cell population. When the cell count of CD4-positive CD8-positive T cells in the human T cell population is relatively low and the T cell population is mainly composed of CD4-positive CD8-dimly positive T cells (B group) and CD4-positive CD8-negative T cells, the population becomes to be the one in the form of general T-helper cells different from the desired T cell population. The percentages of blast cells and of respective groups A to C in the human T cell population can be assayed on flow cytometry using a double stained anti-human CD4-antibody and anti-human CD8-antibody. Since the assay can be easily applied to any occasion after any of the second to the fourth steps in the production method according to the present invention, the examination of percentage of CD4-positive CD8-positive T cells to the total cells of T cell population can be made as an index for determining whether a desired human T cell population is being prepared or not.

The human T cell population, which has both cytotoxic and immunosuppressive activities according to the present invention, exerts cytotoxic activity against the stromal cells used in co-culturing for obtaining the population. In the production method according to the present invention, the complete extinction of the stromal cells used in co-culturing can be macroscopically observed, resulting in an observation of the cytotoxicity against the stromal cells. Apart from the production steps, when the human T cell population obtained in the production method according to the present invention is tested for its cytotoxicity on stromal cells, the ratio (E/T) of the cell count of the human T cell population as effective cells (E) against that of the stromal cells as target cells (T) is at least 1/1, and almost most of the stromal cells, which has been used in preparing the human T cell population, will be extinct (dead).

As disclosed in International Patent Publication No. WO 2007/105797 A1, a human T cell population which has both cytotoxic and immunosuppressive activities also exerts cytotoxic activity on various cells other than stromal cells. In the present invention, the cytotoxic activity on cells other than stromal cells is assayed by using WiDr cell strain derived from human colon cancer. As shown in the later described Examples, the strength cytotoxic activity against WiDr cell strain derived from human colon cancer can be evaluated by assaying viable cells with dye up-take method, etc., using a methylene blue dye after adding the human T cell population as effector cells (E), which has both cytotoxic and immunosuppressive activities obtained by the production method according to the present invention, to WiDr cell strain as target cells (T), and then co-culturing the resulting cells. In practicing such assay in the art, a human T cell population in the form of a conventional T-helper cell (a CD4-positive T cell population prepared by stimulating CD4-positive CD25-negative cells separated from human blood with an anti-human CD3 antibody and an anti-human CD28 antibody, and then culturing and proliferating the resulting cells in the presence of IL-2. Throughout the specification, cells called "conventional T cells", is used as a control; however, the human T cell population, which has both cytotoxic and immunosuppressive activities obtained by the production method according to the present invention, has a significantly higher cytotoxic activity than that of the conventional T cells.

The human T cell population, which has both cytotoxic and immunosuppressive activities obtained by the production method according to the present invention, exerts immunosuppressive activity against activated human T cells. The immunosuppressive activity can be assayed, for example, by allogenic lymphocyte mixed reaction used for assaying immunosuppressive activity of CD4-positive CD25-positive regulatory T cells. The strength of immunosuppressive activity can be determined based on the criterion for immunosuppressive activity of CD4-positive CD25-positive regulatory T cells induced from umbilical cord blood (at least 65% immunosuppressive activity means apparent suppressive activity; and 20 to 65% immunosuppressive activity, low suppressive activity), disclosed by Godfrey et al., Blood, Vol. 104, No. 2, pp. 453-461, 2004. The immunosuppressive activity of the human T cell population, obtained by the production method according to the present invention, can be used for the purpose of relieving diseases curable by inducing immunological tolerance, for example, autoimmune diseases such as rheumatism, type I diabetes mellitus, and Crohn's disease; allergic diseases such as food allergy, pollinosis, and atopic dermatitis; and rejection reactions in transplantation and graft-versus-host-reaction.

As disclosed in International Patent Publication No. WO 2007/105797A1, almost most of the cells in the human T cell population, which has both cytotoxic and immunosuppressive activities obtained by the production method according to the present invention, are positive for cell surface antigens characteristic to T cells such as CD3, CD25, CD28, and T cell antigen receptor $\alpha/\beta$. The cell surface antigens of the human T cell population, obtained by the production method according to the present invention, can be analyzed on flow cytometry using antibodies against surface antigens (indirect immunofluorescence test. Concretely, commercialized mouse anti-human CD3 antibody, mouse anti-human CD25 antibody, mouse anti-human CD28 antibody, or a mouse anti-human T cell antigen receptor $\alpha/\beta$ is added to the human T cell population for 30-min treatment, and in usual manner treating with a secondary antigen (a goat anti-mouse IgG) coupled with fluorescein isothiocyanate (FITC) or phycoerythrin (PE), similarly as above, and then analyzing the resultant on flow cytometry.

As disclosed in International Patent Publication No. WO 2007/105797 A1 and in later described Examples, the human T cell population, which has both cytotoxic and immunosuppressive activities and which is obtained by the production method according to the present invention, produces IL-10 in a culture supernatant when cultured in the presence of IL-2. It is known that IL-10 is a cytokine, which mainly plays a role in immunosuppression, which is produced from T-helper type 2 cells in T cells, and which produces both cytokines such as interferon-$\gamma$ (IFN-$\gamma$) by T-helper type 1 cells and inflammatory cytokines such as IL-1 by macrophages. Accordingly, the human T cell population, which has both cytotoxic and immunosuppressive activities and which is obtained by the production method according to the present invention, is speculated to possibly exert immunosuppressive activity through the production of IL-10.

The human T cell population, which has both cytotoxic and immunosuppressive activities and which is obtained by the production method according to the present invention, contains a cell which expresses transcription factor FOXP3 within the nucleus and which is positive for cytolytic T lymphocyte associated antigen-4 (CTLA-4). It is known that CD4-positive CD25-positive regulatory T cells as a group of cells, which suppress excessive immune reaction such as autoimmune diseases and allergies, specifically express transcription factor FOXP3 and consistently express CTLA-4 at a relatively high level. It is also known that FOXP3 regulates the expression of CTLA-4.

As described later in Examples, both the CD14-positive cells and CD2-positive CD14-negative cells, obtained in the first step in the production method according to the present invention, can be cryopreserved and, if necessary, they can be used in the subsequent culturing steps after thawing. In the case of using CD2-positive CD14-negative cells in the second step without freezing or using them in the second step after being once-cyropreserved and thawed, there is almost no difference between them in terms of percentage of blast cells in the total cells. Nevertheless, since cells are damaged to some extent through freezing and thawing, the count of cells to be inoculated should preferably be set to a relatively higher level when frozen cells are subjected to the next second step.

The following Examples explain the present invention in detail but they do not limit the scope of the present invention. Example 1 explains the production method for the human T cell population which has both cytotoxic and immunosuppressive activities according to the present invention, and Example 2 explains the results of tests on whether the human T cell population, which is prepared by the production method according to the present invention, is a desired human T cell population which has both cytotoxic and immunosuppressive activities. With reference to Example for Reference, both the conventional method disclosed in International Patent Publication No. WO 2007/105797 A1 and the results of judgment on the human T cell population obtained by the method are explained.

EXAMPLE 1

First Step

Preparation of CD14-Positive Cells and CD2-Positive CD14-Negative Cells from Mononuclear Cells Derived from Human Umbilical Cord Blood Umbilical cord bloods, Nos. 1 to 10, were collected from umbilical cords of 10 pregnant women, who had been received an informed consent, at deliveries, and were respectively diluted with RPMI1640 medium at a dilution rate of about two folds and, in usual manner, layered on FICOLL PAQUE™ PLUS (GE Healthcare Biosciences, Tokyo, Japan), and subjected to centrifugal separation. Respective layers containing mononuclear cells were respectively collected and washed with physiological saline to obtain mononuclear cells derived from umbilical cord blood samples (Nos. 1 to 10). To these mononuclear cells thus obtained were respectively applied MACS method, and CD14-positive CD2-positive CD14-negative cells were prepared as follows: The mononuclear cells ($10^7$ cells) in each specimen were dispersed in a phosphate buffered saline (pH 7.2) containing 80 µl of 0.25% calf serum albumin and 2 mM EDTA, admixed with 20 µl of "CD14 MICROBEADS", a product name of microbeads commercialized by Miltenyi Biotec, Tokyo, Japan, which had been magnetized after being coupled with an anti-human CD14 monoclonal antibody, and allowed to stand at 4 to 8° C. for 15 min to effect magnetic-labeling treatment. Thereafter, the cells with magnetic-labeling treatment were admixed with a fresh preparation of the same physiological saline as used in the above, centrifugally washed, dispersed in 500 µl of the same buffer per $10^8$ cells, poured into "LS COLUMN", a product name of a column for MACS method, commercialized by Miltenyi Biotec, Tokyo, Japan, and eluted from the column with the same buffer. The cells free of magnetic labeling, which had been eluted in the above procedure, were collected as CD14-negative cells. The CD14-negative cells thus obtained were treated similarly as above except for dispersing them in 60 µl of the same buffer per $10^7$ cells and successively admixing the cells with FcR blocking reagent commercialized by Miltenyi Biotec, Tokyo, Japan, and 20 µl of "CD2 MICROBEADS", a product name of microbeads coupled with an anti-human CD2 monoclonal antibody, and then magnetized to fractionate them into CD2-positive CD14-negative cells and CD2-negative CD14-negative cells. The resulting CD14-positive cells, Nos. 1 to 10, and CD2-positive CD14-negative cells, Nos. 1 to 10, which had been prepared from the umbilical cord bloods, Nos. 1 to 10, were respectively subjected to culturing of the following second step. FIG. 1 is a figure for typically explaining the first step of the production method according to the present invention as illustrated in this Example.

Second Step 2

Obtention of Blast Cells by Co-Culturing CD2-Positive CD14-Negative Cells with Stromal Cells The CD2-positive CD14-negative cells, Nos. 1 to 10, which had been prepared in the first step, were respectively suspended in RPMI1640 medium supplemented with 10% (v/v) fetal calf serum, and inoculated to commercialized 6-well microplates, which "ST2" (RCB0224, RIKEN BioResource Center, Tsukuba, Japan), a mouse stromal cell strain, had been cultured up to reach a confluent state ($4\times10^5$ mouse stromal cells/well) in the bottom of each well (well's bottom surface of 9.62 cm$^2$) at a cell density of $6\times10^6$ cell/well or $6.2\times10^5$ cells/cm$^2$, based on the bottom surface area of each well. After about one-week of co-culturing, the resulting floating cells were collected along with the culture media for use as human T cell populations, Nos. 1 to 10, each containing blast cells.

<Calculation of Percentages of Blast Cells in Human T Cell Populations, Nos. 1 to 10>

Figure 2:
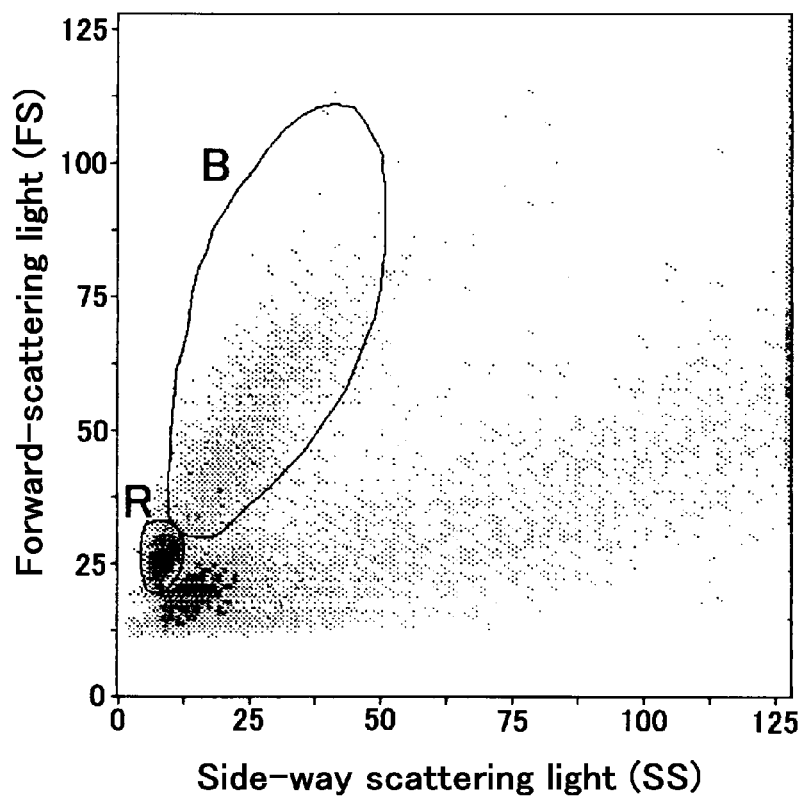
FIG. 2 is a figure for explaining a two-dimensional pattern of forward-scattering light (FS) and side-way scattering light (SS) in flow cytometry for a human T cell population which contains blast cells, obtained by co-culturing CD2-positive CD14-negative cells derived from umbilical cord blood No. 6, with stromal cells.

For the human T cell populations, Nos. 1 to 10, containing blast cells, the blast cells and the cells in resting stage were respectively counted by the following method: The collected human T cell populations were subjected to flow cytometry to analyze their two-dimensional patterns of forward-scattering light (FS) and side-way scattering light (SS). Based on the above cell counts, the percentage of blast cells was calculated with the following formula. As an example of flow cytometry, FIG. 2 is a two-dimensional pattern of FS and SS for human T cell population No. 6 (wherein in FIG. 2, the symbols "B" and "R" mean "blast cells" and "cells in resting stage", respectively, and most of other dots mean cell debris).

$$\text{Percentage of blast cells}(\%) = \left(\frac{A}{B}\right) \times 100 \quad \text{Formula 1}$$

A: Count of blast cells

B: (Count of blast cells)+(Count of cells in resting stage)

<Analysis on Cell-Surface-Antigens, CD4 and CD8, in Human T Cell Population>

Figure 3:
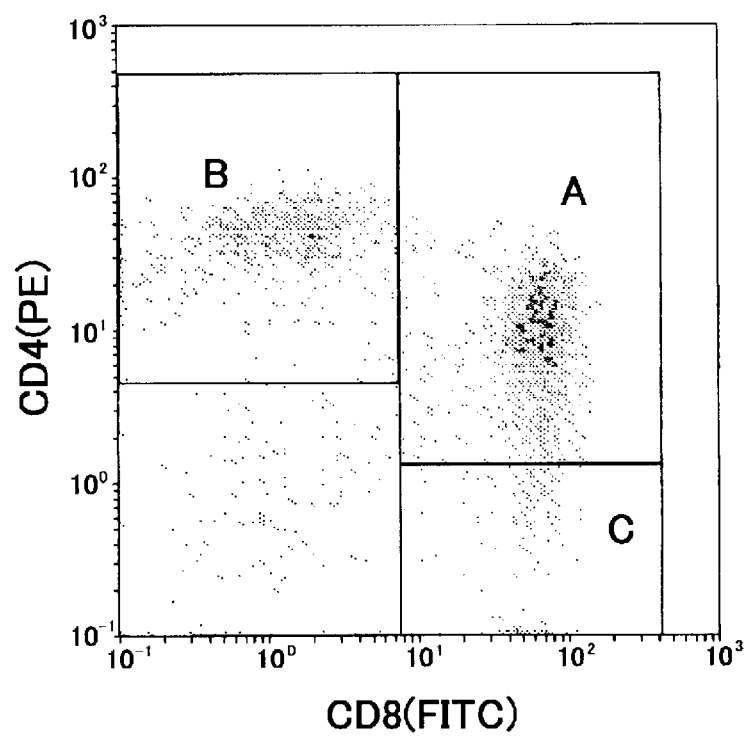
FIG. 3 is a figure for explaining the result from a double-staining flow cytometry for a human T cell population containing blast cells, obtained by co-culturing CD2-positive CD14-negative cells derived from umbilical cord blood No. 6, with stromal cells.

For human T cell populations, Nos. 1 to 10, thus obtained, they were double stained by a mouse anti-CD4 antibody labeled with phycoerythrin (PE) and a mouse anti-human CD8 antibody labeled with fluorescein isothiocyanate (FITC), commercialized by Nippon Becton Dickinson Company, Ltd., Tokyo, Japan, and analyzed on flow cytometry to classify the blast cells into three groups of a CD4-positive CD8-positive cell group, CD4-positive CD8-dimly positive cell group, and CD4-negative CD8-positive cell group. Based on the cell counts, the percentage (%) of cells in respective groups present in the blast cells was determined. As an example of flow cytometry for the human T cell populations obtained in this step, the result of human T cell population No. 6 is shown in FIG. 3 (wherein in FIG. 3, the symbols "A", "B", and "C" means "CD4-positive CD8-positive cells", "CD4-positive CD8-dimly positive cells", and "CD4-negative CD8-positive cells", respectively). The preparation results of blast cells, obtained by co-culturing CD2-positive CD14-negative cells with stromal cells, are tabulated in Table 1.

TABLE 1

| No.* | Culturing period (day) | Induction of blast cells | Percentage of blast cells in total cells (%) | Percentage of each cell group in blast cells (%) | | | Percentage of CD4-positive CD8-positive cells in total cells |
|---|---|---|---|---|---|---|---|
| | | | | A | B | C | |
| 1 | 7 | Yes | 53.4 | 50.9 | 38.7 | 1.9 | 27.2 |
| 2 | 7 | Yes | 53.2 | 73.5 | 20.3 | 1.6 | 39.1 |
| 3 | 8 | Yes | 64.6 | 68.7 | 27.9 | 2.1 | 44.4 |
| 4 | 9 | Yes | 49.3 | 59.9 | 32.1 | 5.5 | 29.5 |
| 5 | 7 | Yes | 50.8 | 49.8 | 42.0 | 2.1 | 25.3 |
| 6 | 7 | Yes | 49.3 | 52.2 | 33.8 | 5.8 | 25.7 |
| 7 | 9 | Yes | 33.9 | 39.7 | 46.5 | 10.0 | 13.5 |
| 8 | 6 | Yes | 32.6 | 41.7 | 39.7 | 10.0 | 13.6 |
| 9 | 8 | Yes | 21.6 | 30.9 | 61.2 | 5.5 | 6.7 |
| 10 | 8 | Yes | 29.4 | 37.9 | 49.7 | 9.3 | 11.1 |

Note:
The symbol "*" corresponds to an umbilical cord blood number (No.).
The symbols "A", "B" and "C" mean "CD4-positive CD8-positive", "CD4-positive CD8-dimly positive", and "CD4-negative CD8-positive", respectively.

The first column heading is: CD2-Positive CD14-negative cells used in co-culturing with stromal cells As shown in Table 1, when CD2-positive CD14-negative cells, which are respectively corresponded to those derived from umbilical cord bloods, Nos. 1 to 10, were co-cultured with stromal cells, blast cells were generated in all the 10 cultures tested in the second step of the production method according to the present invention. The percentage of blast cells in the total cells of each co-culturing system was about 21% to about 64% at the completion of each culture, while the percentage of CD4-positive CD8-positive cells in blast cells was about 30% to about 73%. The percentage of CD4-positive CD8-positive cells in the total cells was about 6.7% to about 44% at the completion of this step.

Third Step

Proliferation of Blast Cells when CD14-Positive Cells as Human T Cell Populations, Nos. 1 to 10, Containing Blast Cells, are Co-Cultured with Mouse Stromal Cells, ST2

CD14-Positive cells derived from umbilical cord bloods, Nos. 1 to 10, which had been prepared in the above-identified first step, were respectively suspended in RPMI1640 medium supplemented with 10% (v/v) fetal calf serum, and inoculated to commercialized 6-well microplates, which "ST2", a mouse stromal cell strain, had been cultured up to reach a confluent state ($4 \times 10^5$ mouse stromal cells/well) in the bottom of each well, at a cell density of $2 \times 10^6$ cells/3 ml per well, and co-cultured for one week. The resulting co-cultures were inoculated with $2 \times 10^6$ cells/3 ml per well of respective human T cell populations, Nos. 1 to 10, containing blast cells, which had been obtained in the above-mentioned second step, and subjected to the following procedure twice in a sequential manner of culturing the cells for two to three days and then transferring the proliferated cells over a fresh mouse stromal cells, ST2, to continue culturing.

After completion of the culture, floating blast cells along with the culture media were collected from respective resulting cultures, which had been cultured by inoculating the human T cell populations, Nos. 1 to 10, to obtain blast cell populations, No. 1 to 10. The cells in each blast cell population were counted in usual manner and the proliferation percentage of blast cells was determined based on the number of cells used in each culture. According to a similar method as used in Example 2, each blast population was classified into three groups of CD4-positive CD8-positive group, CD4-positive CD8-dimly positive group, and CD4-negative CD8-positive group, and the percentage (%) of blast cells for each group was determined based on the number of cells. The results are in Table 2.

TABLE 2

| Blast cell No.* | Culturing period (day) | Inoculated cells ($\times 10^7$ cells) | Collected cells ($\times 10^7$ cells) | Cell proliferation rate (fold) | Percentage of each cell group in blast cells (%) | | |
|---|---|---|---|---|---|---|---|
| | | | | | A | B | C |
| 1 | 7 | 0.92 | 8.70 | 9.4 | 41.6 | 29.4 | 28.6 |
| 2 | 6 | 2.50 | 21.35 | 8.6 | 52.6 | 24.2 | 24.0 |
| 3 | 6 | 1.20 | 9.48 | 7.9 | 29.5 | 40.6 | 28.5 |
| 4 | 7 | 1.71 | 10.28 | 6.0 | 39.6 | 40.6 | 19.2 |
| 5 | 7 | 5.63 | 73.68 | 13.1 | 37.5 | 47.2 | 14.0 |
| 6 | 7 | 1.24 | 9.25 | 7.5 | 40.5 | 25.0 | 27.6 |
| 7 | 7 | 0.71 | 6.32 | 8.9 | 27.4 | 50.9 | 19.8 |
| 8 | 7 | 7.39 | 25.80 | 3.5 | 32.8 | 28.8 | 38.3 |
| 9 | 7 | 3.12 | 34.38 | 11.0 | 11.9 | 66.4 | 19.7 |
| 10 | 7 | 4.24 | 41.04 | 9.7 | 39.1 | 49.2 | 10.9 |

Note:
The symbol "*" corresponds to an umbilical cord blood number (No.).
The symbols "A", "B" and "C" mean "CD4-positive CD8-positive", "CD4-positive CD8-dimly positive", and "CD4-negative CD8-positive", respectively.

Figure 4:
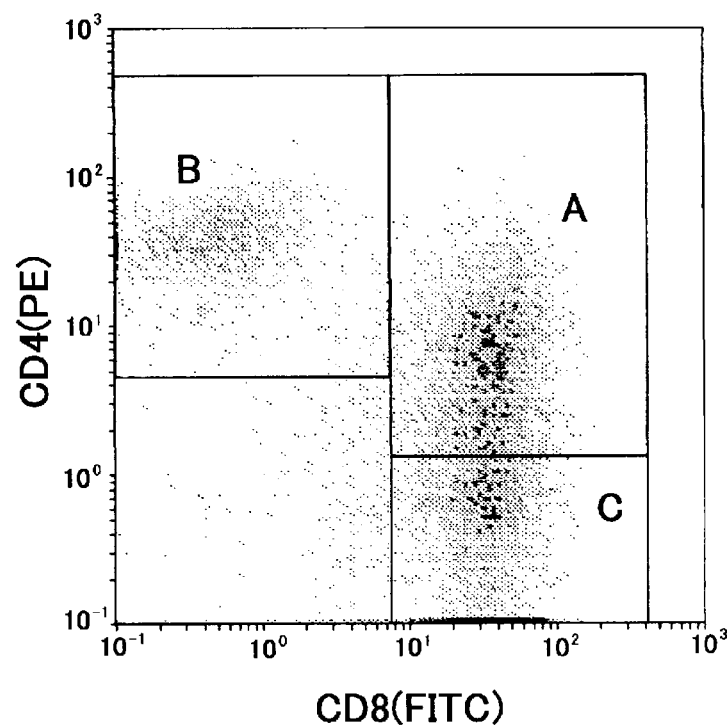
FIG. 4 is a figure for explaining the result from a double-staining flow cytometry for a human T cell population, obtained by co-culturing blast cells derived from umbilical cord blood No. 6, with stromal cells in the presence of IL-2.

As shown in Table 2, the cell proliferation rate of blast cells in this step is 3.5 to 13.1 folds and is 8.6 folds in average. In the previous step, the human T cell population derived from cell population No. 6 is shown in FIG. 4 (wherein in FIG. 4 the meanings of symbols "A", "B" and "C" are the same as those in FIG. 3). The results are in Table 3.

TABLE 3

| Blast cell No.* | Culturing period (day) | Inoculated cell count ($\times 10^7$ cells) | Collected cell count ($\times 10^7$ cells) | Rate of proliferation (fold) | Percentage of each cell group in blast cells (%) | | |
|---|---|---|---|---|---|---|---|
| | | | | | A | B | C |
| 1 | 9 | 0.45 | 28.00 | 62.2 | 39.4 | 20.0 | 35.4 |
| 2 | 8 | 0.43 | 164.40 | 382.3 | 32.8 | 12.5 | 53.4 |
| 3 | 8 | 1.00 | 7.57 | 7.6 | 33.6 | 19.8 | 45.4 |
| 4 | 7 | 0.61 | 10.10 | 16.7 | 34.2 | 29.3 | 36.3 |
| 5 | 10 | 0.51 | 79.34 | 155.6 | 51.4 | 13.6 | 34.3 |
| 6 | 10 | 0.52 | 39.90 | 76.6 | 46.2 | 14.4 | 38.5 |
| 7 | 8 | 0.74 | 18.02 | 24.2 | 35.8 | 34.0 | 29.6 |
| 8 | 9 | 0.50 | 15.30 | 30.6 | 37.6 | 12.2 | 49.5 |
| 9 | 7 | 0.50 | 3.88 | 7.8 | 9.4 | 74.9 | 14.8 |
| 10 | 7 | 0.50 | 16.80 | 33.6 | 35.0 | 14.9 | 47.0 |

Note:
The symbol "*" corresponds to an umbilical cord blood number (No.).
The symbols "A", "B" and "C" mean "CD4-positive CD8-positive", "CD4-positive CD8-dimly positive", and "CD4-negative CD8-positive", respectively.

umbilical cord blood No. 9, which showed a percentage of CD4-positive CD8-positive T cells in the total cells as the lowest level of 9.6%, and marked a lower percentage of 11.9% of CD4-positive CD8-positive T cells against the total cells. Accordingly, the human T cell population derived from the umbilical cord blood No. 9 did not fulfill the requirement of "CD4-positive CD8-positive T cells account for at least 20% of the total cells" defined as a criterion of judgment for a desired human T cell population which has both cytotoxic and immunosuppressive activities. At this stage, those which fulfill the above criterion are nine out of ten umbilical cord bloods.

Fourth Step

Proliferation in Co-Culturing any of Human Blast Cell Populations, Nos. 1 to 10, with Stromal Cells in the Presence of IL-2

The human blast cell populations, Nos. 1 to 10, obtained in the above third step, were respectively suspended in RPMI1640 medium supplemented with 10% (v/v) fetal calf serum and IL-2 (10 ng/ml), and inoculated to commercialized 6-well microplates, which "ST2", a mouse stromal cell strain, had been cultured up to reach a confluent state ($4 \times 10^5$ mouse stromal cells/well) in the bottom of each well, at a cell density of $5 \times 10^6$ cells/3 ml per well. Thereafter, the proliferated cells were subjected to the following procedure twice in a sequential manner of culturing the cells for two to three days and then transferring the proliferated cells over a fresh mouse stromal cells, ST2, to continue the culturing.

After completion of the culture, similarly as the above third step, the cells were collected from respective resulting cultures, which had been cultured with the inoculated blast cells, Nos. 1 to 10, to obtain human T cell populations, No. 1 to 10. The cells in each human T cell population were counted and the proliferation percentage of cells in each human T cell population was determined. According to a similar method as in the above-identified second step, each human T cell population was classified into three groups of a CD4-positive CD8-positive group, CD4-positive CD8-dimly positive group, and CD4-negative CD8-positive group, and the percentage (%) of cells in each group was determined based on the cell count. As an example of flow cytometry for human T cell population obtained in this step, the result of the human T cell population No. 6 is shown in FIG. 4 (wherein in FIG. 4 the meanings of symbols "A", "B" and "C" are the same as those in FIG. 3). The results are in Table 3.

As shown in FIG. 4, the human T cell population obtained in this step consists essentially of CD4-positive CD8-positive T cells (symbol "A" in FIG. 4), CD4-positive CD8-dimly positive T cell (symbol "B" in FIG. 4), and CD4-negative CD8-positive T cells (symbol "C" in FIG. 4), and had an increased percentage of CD4-negative CD8-positive cells than that of the human T cell population as shown in the later stage of the first step (FIG. 3). As shown in Table 3, the cell proliferation rate in this step was 7.6 to 382 folds. The human T cell population No. 9, which had exhibited a low cell count of CD4-positive CD8-positive cells against the total cells in the above-identified second and third steps, gave a cell count as low as 9.4% in terms of a percentage of CD4-positive CD8-positive cells against the total cells (those in human T cell population). Accordingly, the human T cell population No. 9 did not fulfill the above-identified criterion.

Figure 5:
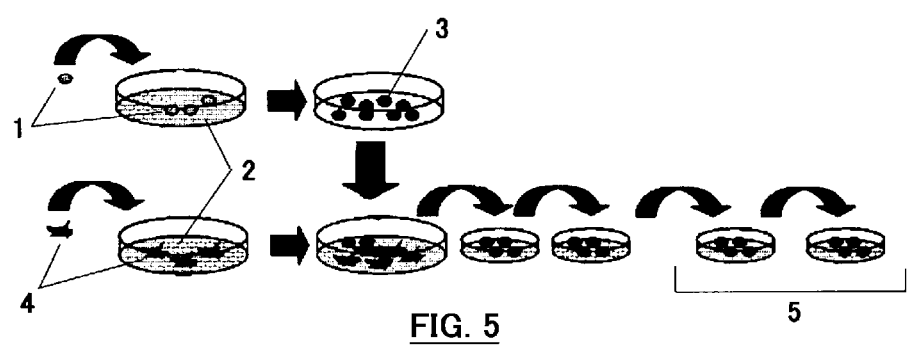
FIG. 5 is a figure for typically explaining the second to the fourth steps in the production method according to the present invention.

The flow chart of the second, third and fourth steps in the production method according to the present invention is typically illustrated in FIG. 5. Explaining again the above three steps with reference to FIG. 5, in the second step (upper part in FIG. 5), the CD2-positive CD4-negative cells (symbol "1" in FIG. 5) obtained in the first step are co-cultured by adding to stromal cells, which have been proliferated up to a confluent state (symbol "2" in FIG. 5), to generate blast cells (symbol "3" in FIG. 5). In the third step, the CD14-positive cells (symbol "4" in FIG. 5), obtained in the first step, is co-cultured with stromal cells and then admixed with the above blast cells or other cells containing the same, followed by proliferating the blast cells while subculturing them. In the fourth step, the blast cells are proliferated by co-culturing (symbol "5" in FIG. 5) with stromal cells in the presence of IL-2 while subculturing them to obtain a human T cell population which has both cytotoxic and immunosuppressive activities.

EXAMPLE 2

The following criteria were set up to judge whether a human T cell population, which had been prepared by the fourth step in Example 1, is the objective human T cell population which has both cytotoxic and immunosuppressive activities, disclosed in International Patent Publication No.

WO 2007/105797 A1. When the human T cell population fulfills all the criteria, it was judged to be an objective human T cell population.
(1) CD4-Positive CD8-positive T cells account for at least 20% of the total cells;
(2) It exhibits cytotoxic activity against stromal cells that have been used in co-culturing;
(3) It exhibits cytotoxic activity against WiDr cell strain derived from human colon cancer;
(4) It has immunosuppressive activity against activated T cells;
(5) It is positive for cell-surface-antigens CD3, CD25 and CD28, as well as T cell antigen receptor α/β; and
(6) It produces IL-10 in the presence of IL-2.

Among the above items, since the item (1) has been already confirmed in Example 1 and the item (2) has been confirmed that stromal cells were macroscopically observed their extinction (death) and cytotoxicity when the human T cell population was co-cultured with the stromal cells in the fourth step of Example 1, the human T cell populations, Nos. 1 to 10, obtained in the fourth step in Example 1, were examined whether they fulfill the above-identified items (3) to (6) in the following experiments.

<Cytotoxic Activity Against WiDr Cell Strain Derived from Human Colon Cancer>

The cytotoxic activity against WiDr cell strain derived from human colon cancer (JRCB0224, Health Science Research Resources Bank, Osaka, Japan) was evaluated by assaying viable cells with dye uptake method using methylene blue: Cells of WiDr cell strain were suspended in RPMI1640 medium supplemented with 10% (v/v) fetal calf serum (FCS), and the cell suspension was placed in 48-well microplates, which had been treated with gelatin, at a cell concentration of $4 \times 10^4$ cells/well, followed by culturing overnight. To the resulting culture of WiDr cell strain as target cells (T) was added any one of the human T cell populations, Nos. 1 to 10, obtained in the first to fourth steps in Example 1, as effector cells (E), at a ratio (E:T) of 8:1, followed by initiating the co-culture (medium: RPMI1640 supplemented with 10% FCS and 10 ng/ml of IL-2). After 20 hours of co-culturing, the effector cells and death cells were removed from the resulting culture, which was then admixed with 400 µl of medium (RPMI1640 supplemented with 10% FCS). The resulting culture was admixed with one drop of 25% glutaraldehyde solution (Wako Pure Chemical Industries, Ltd., Osaka, Japan) with a Pasteur pipette to be immobilized for 15 min, washed with water, and dried. The dried resultant was admixed with 200 µl of 0.1% methylene blue (Wako Pure Chemical Industries, Ltd., Osaka, Japan), stained for 15 min, washed with water, and dried. Finally, the resultant was admixed with 200 µl of 0.33-N HCl to elute methylene blue, and 200 µl of the resulting extract was collected and transferred to 96-well plates and measured for absorbance at a wavelength of 650 nm on "Vmax PLATE READER", a product name of absorptiometer, commercialized by Wako Pure Chemical Industries, Ltd., Osaka, Japan, followed by calculating the cytotoxic activity (%) by the following Formula 2. In Formula 2, the term "Co-culture value" means an absorbance of a culture of WiDr cell strain co-cultured with a human T cell population, and the term "Sole culture blue of WiDr cell strain" means the absorbance of a culture of WiDr cell strain without addition of any human T cell population as effector cells (E), and the term "Blank value" means an absorbance of a culture similarly treated as above without inoculation of any cells. In this assay, conventional T cells (a CD4-positive T cell population prepared by culturing and proliferating CD4-positive CD25-negative cells, which had been separated from a human blood and stimulated with an anti-human CD3 antibody and anti-human CD28 antibody, in the presence of IL-2) were used as a control and measured for cytotoxic activity similarly as above. The results are in Table 4.

$$\text{Cytotoxic activity}(\%) = 100 - \left( \frac{\text{(Co-culture value)} - \text{(Blank value)}}{\text{(Sole culture value of } WiDr \text{ cell strain)} - \text{(Blank value)}} \right) \times 100 \quad \text{Formula 2}$$

TABLE 4

| Human T cell population No.* | Cytotoxic activity against WiDr cell strain derived from human colon cancer (%) |
|---|---|
| 1 | 39.3 |
| 2 | 97.7 |
| 3 | 99.5 |
| 4 | 99.5 |
| 5 | 99.9 |
| 6 | 96.2 |
| 7 | 82.4 |
| 8 | 73.0 |
| 9 | 85.9 |
| 10 | 80.0 |
| Conventional T cell (Control) | 12.4 |

Note:
The symbol "*" corresponds to an umbilical cord blood number (No.).

As shown in Table 4, the cytotoxic activity (%) of conventional T cells, as a control, against WiDr cell strain derived from human colon cancer, was 12.4%, and it was judged that those which have a significantly higher value than the above value, i.e., 50% or more, have cytotoxic activity. Since all the human T cell populations, Nos. 2 to 10, showed at least 73% of cytotoxic activity against WiDr cell strain derived from human colon cancer, they were judged to have cytotoxic activity against WiDr cell strain. The human T cell population No. 1 showed a higher cytotoxic activity as high as 39.3% than conventional T cells, however, the value was below the standard value.

<Immunosuppressive Activity>

According to conventional allogenic lymphocyte mixed reaction, the human T cell populations, Nos. 1 to 10, were assayed for their immunosuppressive activities.

CD4-Positive CD25-negative T cells as responsive cells were prepared by the following method: Mononuclear cells were collected from a human peripheral blood by conventional density-gradient-centrifugation using FICOLL-PAQUE™ PLUS density separatory liquid for lymphocytes. CD25-Positive cells in the mononuclear cells were removed to collect CD25-negative cells by applying MACS method using microbeads coupled with an anti-human CD25 monoclonal antibody, commercialized by Miltenyi Biotec, Tokyo, Japan. CD4-Positive cells were collected from the resulting CD25-negative cells by applying MACS method using microbeads coupled with an anti-human CD4 monoclonal antibody, commercialized by Miltenyi Biotec, Tokyo, Japan.

Dendritic cells as stimulating cells were prepared by the following method: By applying MACS method using "HUMAN CD14 MICROBEADS", commercialized by Miltenyi Biotec, Tokyo, Japan, CD14-positive mononuclear cells were collected from a human umbilical cord blood and cultured for one to two weeks in the presence of granulocytemacrophage colony stimulating factor (GM-CSF) and interleukin-4 (IL-4), followed by collecting dendritic cells, culturing them with a lipopolysaccharide for two days, and treating the resulting cells with mitomycin C in usual manner just before subjecting them to allogenic lymphocyte mixed reaction.

The above responsive cells and stimulating cells were respectively inoculated to wells in microplates at respective amounts of $1\times10^5$ cells and $5\times10^3$ cells, followed by inoculating to the mixture cells any one of the human T cell populations, Nos. 1 to 10, at respective amounts of $1\times10^5$ cells, and culturing the resultant for seven days. At 16 hours before completion of the culture, an adequate amount of $^3$H-thymidine was added to each well of the microplates for use as test wells. As control wells, wells similarly treated as above, except for adding none of the human T cell populations, were provided. According to conventional manner, the uptake amounts of $^3$H-thymidine in the test and control wells were measured, and the immunosuppressive activities (%) of the wells were calculated by the following Formula 3. The immunosuppressive activities were judged based on the criteria for immunosuppressive activity of CD4-positive CD25-positive regulatory T cells induced from an umbilical cord blood, disclosed by Godfrey et al., "*Blood*", Vol. 104, No. 2, pp. 453-461, 2004, wherein the criteria are as follows: At least 65% immunosuppressive activity means apparent suppressive activity, and 20 to 65% immunosuppressive activity, low suppressive activity. The results are in Table 5.

$$\text{Immunosuppressive activity}(\%) = \left(1 - \frac{\text{Uptake amount of }^3\text{H-thymidine of test well (cpm)}}{\text{Uptake amount of }^3\text{H-thymidine of control well (cpm)}}\right) \times 100 \quad \text{Formula 3}$$

TABLE 5

| Human T cell population No.* | Immunosuppressive activity (%) |
|---|---|
| 1 | 83.1 |
| 2 | 91.4 |
| 3 | 97.8 |
| 4 | 88.2 |
| 5 | 98.8 |
| 6 | 98.6 |
| 7 | 83.5 |
| 8 | 93.4 |
| 9 | 98.7 |
| 10 | 93.6 |

Note:
The symbol "*" corresponds to an umbilical cord blood number (No.).

As shown in Table 5, since all the 10 human T cell populations, Nos. 1 to 10, obtained in the fourth step in Example 1, showed immunosuppressive activities of 65% or more, they were judged to have distinct immunosuppressive activities.

<Analysis on Cell-Surface-Antigens CD3, CD25 and CD28, and T Cell Antigen Receptor α/β>

The human T cell populations, Nos. 1 to 10, obtained in the fourth steps in Example 1, were analyzed on flow cytometry using an anti-human CD3 antibody (commercialized by R & D Systems, Inc., Tokyo, Japan), anti-human CD25 antibody (commercialized by Beckman Coulter, Inc., Tokyo, Japan), and anti-human T cell antigen receptor α/β (commercialized by Nippon Becton Dickinson Company, Ltd., Tokyo, Japan), respectively. As a negative control, MOPC-21 mouse myeloma IgG (commercialized by ICN Biomedicals, Inc., CA, USA) was used. Test cells were treated with any of the above antibodies for 30 min and in usual manner further treated with a secondary antibody (a goat anti-mouse IgG) coupled with fluorescein isothiocyanate (FITC) for 30 min. The test cells were analyzed on "EPICS XL", a product name of flow cytometer commercialized by Beckman Coulter, Inc., Tokyo, Japan, and the results are in Table 6. The positive percentage (%) means a ratio of cells, among the test cells, which show a fluorescent strength not lower than the threshold settled based on that of the negative control. As for CD3 and T cell antigen receptor α/β which are indexes for T cells, those which have positive percentages (%) of 90% or more are judged to be positive, similarly as in the human T cell populations which have both cytotoxic and immunosuppressive activities, disclosed in International Patent Publication No. WO 2007/105797 A1. As for CD25 and CD28, those which have positive percentages (%) of 70% or more are judged to be positive.

TABLE 6

| Human T cell population No.* | Positive percentage of cell surface antigen CD3 (%) | Positive percentage of T cell antigen receptor α/β (%) | Positive percentage of cell surface antigen CD25 (%) | Positive percentage of cell surface antigen CD28 (%) |
|---|---|---|---|---|
| 1 | 99.7 | 99.3 | 81.8 | 71.5 |
| 2 | 99.8 | 99.0 | 95.9 | 89.6 |
| 3 | 99.8 | 99.4 | 94.7 | 99.3 |
| 4 | 100.0 | 98.7 | 86.7 | 91.8 |
| 5 | 99.1 | 99.2 | 81.5 | 77.4 |
| 6 | 99.6 | 98.2 | 81.5 | 96.8 |
| 7 | 98.2 | 97.4 | 89.8 | 76.7 |
| 8 | 99.8 | 98.6 | 96.9 | 85.0 |
| 9 | 99.2 | 98.7 | 80.8 | 86.0 |
| 10 | 100.0 | 99.0 | 92.9 | 99.6 |

Note:
The symbol "*" corresponds to an umbilical cord blood number (No.).

As shown in Table 6, all the 10 human T cell populations, Nos. 1 to 10, obtained in the fourth step in Example 1, showed positive percentages of cell-surface-antigen CD3 of 98.2% or more, positive percentages of T cell antigen receptor α/β of 98.2% or more, positive percentages of CD25 of 80.8% or more, and positive percentages of CD28 of 71.5% or more; and based on these they were judged to be positive for cell-surface-antigens CD3, CD25 and CD28, as well as T cell antigen receptor α/β.

<IL-10 Productivity in the Presence of IL-2>

IL-10 Productivity in the presence of IL-2 by the human T cell populations, Nos. 1 to 10, were determined by using the culture supernatants obtained from the cultures of the human T cell populations in the fourth step in Example 1, and assaying the IL-10 concentrations in the supernatants with an assay kit using an anti-human IL-10 antibody, produced by eBioscience, Inc., CA, USA. In this assay, considering conventional T cells well used as a control in this field produce about 30 pg/ml of IL-10, those which had produced a significantly higher level of IL-10 as high as 100 pg/ml or more in culture media were judged to have IL-10 productivity. The results are in Table 7.

TABLE 7

| Human T cell population No.* | Concentration of IL-10 in culture supernatant (pg/ml) |
| --- | --- |
| 1 | 86.0 |
| 2 | 721.9 |
| 3 | 874.8 |
| 4 | 797.6 |
| 5 | 1469.0 |
| 6 | 6815.0 |
| 7 | 744.4 |
| 8 | 2715.0 |
| 9 | 5287.0 |
| 10 | 2497.0 |

Note:
The symbol "*" corresponds to an umbilical cord blood number (No.).

As evident from Table 7, all the human T cell populations, Nos. 2 to 10, excluding No. 1, produced IL-10 in their culture supernatants at concentrations of 700 pg/ml or more, meaning that nine out of ten populations fulfilled the above criterion of IL-10 productivity.

<Comprehensive Judgment>

Based on the results obtained in the above experiments, the human T cell populations, Nos. 1 to 10, obtained in the fourth step in Example 1, were totally judged whether they are the desired human T cell populations which have both cytotoxic and immunosuppressive activities. The results are tabulated in Table 8. In Table 8, the symbols "○" and "x" represent that "it fulfills the criteria for judgments" and "it does not", respectively.

TABLE 8

| Items of Judgment | Human T cell population No.* | | | | | | | | | |
| --- | --- | --- | --- | --- | --- | --- | --- | --- | --- | --- |
| | 1 | 2 | 3 | 4 | 5 | 6 | 7 | 8 | 9 | 10 |
| Percentage of CD4-positive and CD8-positive T cells in blast cells | ○ | ○ | ○ | ○ | ○ | ○ | ○ | ○ | x | ○ |
| Cytotoxic activity against stromal cells | ○ | ○ | ○ | ○ | ○ | ○ | ○ | ○ | ○ | ○ |
| Cytotoxic activity against WiDr cell strain derived from human colon cancer | X | ○ | ○ | ○ | ○ | ○ | ○ | ○ | ○ | ○ |
| Immunosuppressive activity | ○ | ○ | ○ | ○ | ○ | ○ | ○ | ○ | ○ | ○ |
| Positive for cell-surface-antigens CD3, CD25 and CD28, and T cell antigen receptor α/β | ○ | ○ | ○ | ○ | ○ | ○ | ○ | ○ | ○ | ○ |
| Interleukin-10 (IL-10) productivity | X | ○ | ○ | ○ | ○ | ○ | ○ | ○ | ○ | ○ |
| Comprehensive judgment | X | ○ | ○ | ○ | ○ | ○ | ○ | ○ | X | ○ |

Note:
The symbol "*" corresponds to an umbilical cord blood number (No.).

As evident from Table 8, since the human T cell populations, Nos. 2 to 8 and No. 10, obtained in the fourth step in Example 1, fulfilled the criteria on all the six items of judgment, they were judged to be the desired human T cell populations which have both cytotoxic and immunosuppressive activities. While, the human T cell population No. 1 did not fulfill the criterion on IL-10 productivity and on cytotoxic activity against WiDr cell strain derived from human colon cancer, and the human T cell population No. 9 did not fulfill the criterion for the percentage of CD4-positive CD8-positive T cells in blast cells. Based on these, it was revealed that eight human T cell populations which had both cytotoxic and immunosuppressive activities were obtained from among the 10 umbilical cord bloods, revealing that the provability of obtaining a desired human T cell population which has both cytotoxic and immunosuppressive activities is as high as 80%. The expressions of both nuclear FOXP3 and intracellular CTLA-4 in the human T cell populations, Nos. 2 to 8 and 10, were analyzed similarly as in International Patent Publication No. WO 2007/105797 A1, revealing that all the above populations were judged to have positively expressed them and were substantially the same human T cell populations as those which have both cytotoxic and immunosuppressive activities, disclosed in International Patent Publication No. WO 2007/105797 A1.

EXAMPLE FOR REFERENCE

<Conventional Preparation of Human T Cell Population which has both Cytotoxic and Immunosuppressive Activities from Mononuclear Cells Derived from Human Umbilical Cord Blood>

Umbilical cord bloods, Nos. 1' to 10', were collected from umbilical cords of 10 pregnant women at their deliveries, who had been received an informed consent, and were respectively diluted with RPMI1640 medium at a dilution rate of about two times and, in usual manner, layered on FICOLL-PAQUE™ PLUS density separatory liquid, and subjected to, specific gravity centrifugal separation. Respective layers containing mononuclear cells were respectively collected and washed with physiological saline to obtain mononuclear cells. The mononuclear cells thus obtained were suspended in RPMI1640 medium supplemented with 10% (v/v) fetal calf serum, and the cell suspension was inoculated to commercialized 6-well microplates, which "ST2" (RCB0224, RIKEN BioResources, Tsukuba, Japan), a mouse stromal cell strain, had been cultured up to reach a confluent state ($4 \times 10^5$ mouse stromal cells/well) in the bottom of each well, at a cell density of $3 \times 10^6$ cells/well. After one-week culture, the resulting floating cells were collected along with the culture medium, transferred to 6-well microplates to which fresh stromal cells were adhered, and further co-cultured. The cells were cultured for at least three weeks in total by sequentially repeating the above procedure to generate proliferative blast cells in the form of a homogenous T cell, and admixed with IL-2 to give a final concentration of 10 ng/ml to allow the cells to proliferate, at the time when the culture period was over four weeks. The resulting cells were examined for generation of blast cells by applying a similar method as used in the above, and the percentage of CD4-positive CD8-positive T cells in the generated blast cells was determined by flow cytometry similarly as in Example 1. The results are in Table 9.

TABLE 9

| Umbilical cord blood No. | Culturing period (day) | Induction of blast cell | Percentage of CD4-positive CD8-positive cells in the total cells (%) |
| --- | --- | --- | --- |
| 1' | 24 | No | —* |
| 2' | 31 | Yes | 39.7 |
| 3' | 30 | Yes | 4.9 |
| 4' | 29 | Yes | 9.3 |
| 5' | 27 | Yes | 5.4 |
| 6' | 27 | Yes | 9.2 |
| 7' | 29 | Yes | 4.0 |
| 8' | 25 | No | —* |
| 9' | 25 | Yes | 13.5 |
| 10' | 24 | Yes | 10.9 |

Note:
The symbol "*" means "not measured".

As shown in Table 9, no generation of blast cell was in itself observed from two out of ten umbilical cord bloods, i.e., mononuclear cells derived from the umbilical cord bloods, Nos. 1' and 8'. Although the generation of blast cells from mononuclear cells derived from the umbilical cord bloods, Nos. 3' to 7', 9' and 10', the percentage of CD4-positive CD8-positive T cells in the cells was less than 20% and any of the resulting cells did not fulfill the desired human T cell population which has both cytotoxic and immunosuppressive activities. At this stage, only the human T cell population derived from the umbilical cord blood No. 2' turned out to be the one that fulfills the criteria. The human T cell population derived from umbilical cord blood No. 2' fulfilled all the following criteria when examined by the same method as in Example 2 on the above-mentioned criteria for judgment; (3) cytotoxic activity against WiDr cell strain derived from human colon cancer, (4) immunosuppressive activity, (5) cell-surface-antigens CD3, CD25 and CD28, and T cell antigen receptor α/β, and (6) IL-10 productivity. The result revealed in this Example for Reference, which indicates that conventional method disclosed in International Patent Publication No. WO 2007/105797 A1 could only generate a desired human T cell population having both cytotoxic and immunosuppressive activities at a rate of only one out of ten populations, clearly shows that such conventional method is the one with a relatively-poor efficiency as low as 10% in obtaining a desired human T cell population, even if such a population is obtainable.

The following Example 3 explains the influence of the cell count of CD2-positive CD14-negative cells on the second step of the present invention, and Examples 4 and 5 explain the influence of cryopreservation of CD2-positive CD14-negative cells and CD14-positive cells, obtained in the first step of the production method according to the present invention.

EXAMPLE 3

<Influence of the Cell Count of CD2-Positive CD14-Negative Cells on the Second Step in the Production Method According to the Present Invention>

It was examined the influence of the cell count of CD2-positive CD14-negative cells on the second step of the production method according to the present invention, i.e., the step for inducing blast cells by co-culturing CD2-positive CD14-negative cells with stromal cells.

Using the same method as in Example 1, mononuclear cells and CD2-positive CD14-negative cells were prepared from the umbilical cord blood No. T1 collected from a pregnant woman, who had been received an informed consent. To microplates (a volume of three milliliters and a bottom surface area of 9.62 cm² per well), which mouse stromal cells, ST2, had been proliferated up to reach a confluent state, were inoculated CD2-positive CD14-negative cells at a cell density of $2.0 \times 10^6$ cells or $6.0 \times 10^6$ cells, or $2.1 \times 10^5$ cells/cm² or $6.2 \times 10^5$ cells/cm², based on the bottom surface area of each well. The resulting cells were cultured for eight days, followed by collecting the resulting floating cells along with the culture medium and determining the percentage of the blast cells in the total cells and the percentage of respective cell groups of CD4-positive CD8-positive cells, CD4-positive CD8-dimly positive cells, and CD4-negative CD8-positive cells in the blast cells. The results are in Table 10.

TABLE 10

| Umbilical cord blood No. | | T1 | |
|---|---|---|---|
| Cell density of CD2-positive CD14-negative cells per the bottom surface area of well (×10⁵ cells/cm²) | | 6.2 | 2.1 |
| Culture period (day) | | 8 | 8 |
| Induction of blast cells | | Yes | Yes |
| Percentage of blast cells in the total cells (%) | | 61.8 | 28.6 |
| Percentage of each cell group in blast cells | CD4-Positive CD8-positive | 72.4 | 53.1 |
| | CD4-Positive CD8-dimly positive | 24.7 | 34.0 |
| | CD4-Negative CD8-positive | 0.4 | 9.2 |
| Percentage of CD4-positive CD8-positive cells in the total cells | | 44.7 | 16.9 |

As evident from Table 10, when the CD2-positive CD14-negative cells are inoculated to a microplate at a cell density of $2.1 \times 10^5$ cells/cm² in terms of the bottom area per well, the percentages of blast cells in the total cells and that of CD4-positive CD8-positive cells in the total cells were respectively, relatively low as 28.6% and 16.9%. While, when the CD2-positive CD14-negative cells are inoculated to the microplate at a cell density of $6.2 \times 10^5$ cells/cm² in terms of the bottom area per well, the percentages of blast cells in the total cells and that of CD4-positive CD8-positive cells in the total cells were respectively relatively high as 61.8% and 44.7%. These results indicate that CD2-positive CD14-negative cells should preferably be inoculated at a relatively high cell-density of $6.2 \times 10^5$ cells/cm² in terms of the bottom area per well in order to efficiently induce blast cells and CD4-positive CD8-positive cells in the blast cells.

EXAMPLE 4

<Influence of the Cryopreservation of CD2-Positive CD14-Negative Cells on the Induction of Blast Cells>

It was examined the influence of the cryopreservation of CD2-positive CD14-negative cells, which had been prepared from the first step in the production method of the present invention on the induction of blast cells.

According to the same method as in Example 1, mononuclear cells were prepared from umbilical cord bloods (Nos. S1, S2 and S3), which had been collected from three pregnant women who had had been received an informed consent, and CD2-positive CD14-negative cells were prepared from the mononuclear cells. The obtained CD2-positive CD14-negative cells were divided into two groups; one was directly subjected to a co-culture with stromal cells and the other was dispersed in CELLBANKER® solution for cell preservation, commercialized by JUJI Field, Inc., Tokyo, Japan, frozen at −80° C. overnight for 24 hours, and then subjected to storage under −196° C. (liquid nitrogen). After 12-, 69-, or 94-days of cryopreservation, the cells were quicldy thawed in a warm-bath at 37° C., and subjected to culturing in the second step similarly as above. After about one-week co-culture with stromal cells in the second step, the floating cells were collected along with the culture medium, followed by determining on the method in Example 2 the percentages of respective cell groups of blast cells in the total cells, CD4-positive CD8-positive cells in the blast cells, as well as CD4-positive CD8-dimly positive cells, and CD4-negative CD8-positive cells in the blast cells. Tables 11 shows the influence of handling of cryopreservation for CD2-positive CD14-negative cells on the induction of blast cells.

TABLE 11

| Umbilical cord No. | Cryopreservation in the first step (preservation day) | Culturing period (day) | Induction of blast cells | Percentage of blast cells in total cells (%) | Percentage of each cell group in blast cells (%) | | | Percentage of CD4-positive CD8-positive cells (%) |
|---|---|---|---|---|---|---|---|---|
| | | | | | A | B | C | |
| S1 | No | 8 | Yes | 35.2 | 50.7 | 36.2 | 8.9 | 17.0 |
| | Yes (69 days) | 8 | Yes | 33.9 | 39.7 | 46.5 | 10.0 | 12.3 |
| S2 | No | 8 | Yes | 22.0 | 49.4 | 28.0 | 16.4 | 11.8 |
| | Yes (94 days) | 8 | Yes | 23.7 | 27.5 | 44.1 | 24.0 | 6.9 |
| S3 | No | 8 | Yes | 53.2 | 73.5 | 20.3 | 1.6 | 39.1 |
| | Yes (12 days) | 8 | Yes | 56.8 | 68.2 | 19.4 | 10.0 | 36.1 |

Note:
The symbols "A", "B" and "C" mean "CD4-positive CD8-positive", "CD4-positive CD8-dimly positive", and "CD4-negative CD8-positive", respectively.

As shown in Table 11, when the cryopreserved CD2-positive CD14-negative cells were subjected to co-culturing with stromal cells in the second step, the percentage of blast cells in the total cells in all the tested three umbilical cord bloods were substantially the same as that with CD2-positive CD14-negative cells without cryopreservation. In the case of using cryopreserved CD2-positive CD14-negative cells, there was found a tendency of slight reduction in the percentage of CD4-positive CD8-positive cells in the blast cells compared with that with CD2-positive CD14-negative cells without cryopreservation in all the three cases, resulting in a finding of cytotoxic activity by freezing or thawing. However, it was revealed that there was found no affect on the culture, when a relatively larger number of cells are subjected to the following third step.

EXAMPLE 5

<Influence of the Cryopreservation of CD2-Positive CD14-Negative Cells and CD14-Positive Cells on the Induction of Blast Cells>

Both of the CD2-positive CD14-negative cells and the CD14-positive cells, which had been prepared in the first step in the production method of the present invention, were cryopreserved and thawed to examine the influence of cryopreservation on the induction of blast cells in the second step and on the proliferation of blast cells in the third step, when used after thawing.

According to the same method as in Example 1, mononuclear cells were respectively prepared from the umbilical cord blood No. N1, which had been collected from a pregnant woman who had had been received an informed consent, and both of CD2-positive CD14-negative cells and CD14-positive cells were respectively prepared from the mononuclear cells. The obtained CD2-positive CD14-negative cells and CD14-positive cells were respectively dispersed in CELL-BANKER®, a cell preservation solution, commercialized by JUJI Field, Inc., Tokyo, Japan, frozen at −80° C. overnight, and then after 24 hours subjected to storage under −196° C. (liquid nitrogen). After 90 days of cryopreservation, the cells were quickly thawed in a warm-bath at 37° C., and the CD2-positive CD14-negative cells were subjected to the second step similarly as in Example 4, and CD14-positive cells were subjected to the third step similarly as in Example 1. After about one-week co-culturing with stromal cells in the second step, the floating cells containing blast cells were collected along with the culture medium, followed by determining by the method in Example 2 the percentages of blast cells in the total cells and of respective cell groups of CD4-positive CD8-positive cells, CD4-positive CD8-dimly positive cells, and CD4-negative CD8-positive cells in the blast cells, resulting in 34.8%, 42.7%, 48.3%, and 6.2%, respectively. Thereafter, the human cells containing the blast cells obtained in the above were added to a culture, which had been prepared by co-culturing stromal cells, ST2, with CD14-positive cells which had had been cryopreserved and thawed, for about one week; subjected to culturing under the same conditions as the third step in Example 1, followed by determining the cell proliferation rate of the obtained blast cells and the percentages of respective cell groups of CD4-positive CD8-positive cells in the blast cells, CD4-positive CD8-dimly positive cells, and CD4-negative CD8-positive cells. The results are in Table 12.

TABLE 12

| | | |
|---|---|---|
| Umbilical cord blood No. | | N1 |
| Culturing period (day) | | 7 |
| Inoculated cell count (×10⁷ cells) | | 0.83 |
| Collected cell count (×10⁷ cells) | | 6.16 |
| Cell proliferation rate (fold) | | 7.4 |
| Percentage of each cell group in blast cells (%) | CD4-Positive CD8-positive | 29.5 |
| | CD4-Positive CD8-dimly positive | 45.8 |
| | CD4-Negative CD8-positive | 24.7 |

As evident from Table 12, both of the CD2-positive CD14-negative cells and CD14-positive cells, which had been prepared in the first step, were cryopreserved, and after 90 days of cryopreservation, the cells were thawed and subjected to culturing in the second and third steps, revealing that the parentage of the resulting CD4-positive CD8-positive cells in the resulting blast cells was 29.5%, meaning that the level is substantially the same as in the case of culturing the cells without cryopreservation.

The results in Examples 4 and 5 indicate that any of the CD2-positive CD14-negative cells, prepared in the first step in the production method of the present invention, can be cryopreserved, and they can be used in the culture of the second and third steps in the production method of the present invention after thawing, if necessary. The production method according to the present invention has an advantage of that, unlike conventional method, it does not necessarily require any fresh human umbilical cord blood at every time when preparing the desired human T cell population which has both cytotoxic and immunosuppressive activities.

INDUSTRIAL APPLICABILITY

As explained above, the method for producing a human T cell population, which has both cytotoxic and immunosuppressive activities according to the present invention, efficiently produces a desired human T cell population with such activities useful for treatment of autoimmune diseases and allergic diseases, medical transplantation, cancer treatment, etc. The present invention with such an outstanding effects and functions is a significant invention that will greatly contribute to this art.

EXPLANATION OF SYMBOLS

In FIG. 2, wherein the symbols mean as follows:
B: Blast cells
R: Cells in resting stage
In FIGS. 3 and 4, wherein the symbols mean as follows:
A: CD4-Positive CD8-positive T cells
B: CD4-Positive CD8-dimly positive T cells
C: CD4-Negative CD8-positive T cells
In FIG. 5, wherein the symbols mean as follows:
1: CD2-Positive CD14-negative cells
2: Stromal cells
3: Blast cells
4: CD14-Positive cells
5: Co-culturing with stromal cells in the presence of IL-2

The invention claimed is:

1. A method for producing a human T cell population which has both cytotoxic and immunosuppressive activities, said method comprising the following steps (1) to (5):

(1) fractionating mononuclear cells collected from a human umbilical cord blood into CD14-positive (CD14$^+$) cells and CD14-negative (CD14) cells, and then fractionating the CD14-negative (CD14) cells into CD2-positive CD14-negative (CD2' CD14) cells, and CD2-negative CD14-negative (CD2$^-$CD14) cells;

(2) co-culturing the CD2-positive CD14-negative (CD2$^+$CD14) cells obtained in step (1) with stromal cells to differentiate the CD2-positive CD14-negative (CD2$^+$CD14$^-$) cells into blast cells which have both cytotoxic and immunosuppressive activities;

(3) co-culturing the CD14-positive (CD14$^+$) cells obtained in step (1) with fresh stromal cells to differentiate the CD14-positive (CD14$^+$) cells into cells capable of promoting the proliferation of the blast cells;

(4) adding the blast cells obtained in step (2) to the resulting co-culture of step (3) to proliferate the blast cells obtained in step (2); and (5) co-culturing the blast cells obtained in step (4) with fresh stromal cells in medium supplemented with interleukin-2 (IL-2) to further proliferate, thereby producing a human T cell population which has both cytotoxic and immunosuppressive activities.

2. The method of claim 1, wherein in co-culturing with said stromal cells step (2), said CD2-positive CD14-negative (CD2$^+$CD14$^-$) cells are inoculated at a cell density of 6.2×10$^5$/cm$^2$ in terms of the bottom surface area of each well.

* * * * *